United States Patent
Lu et al.

(10) Patent No.: US 11,058,612 B2
(45) Date of Patent: Jul. 13, 2021

(54) MULTISTAGE COLORED POLYMER PARTICLE AND SKIN CARE FORMULATIONS COMPRISING SAME

(71) Applicant: Rohm and Haas Company, Collegeville, PA (US)

(72) Inventors: Xiaodong Lu, North Wales, PA (US); Xiang Qian Liu, Collegeville, PA (US); Fanwen Zeng, Audubon, PA (US); Junsi Gu, Malvern, PA (US); Wen-Shiue Young, Lansdale, PA (US)

(73) Assignee: Rohm and Haas Company, Collegeville, PA (US)

( * ) Notice: Subject to any disclaimer, the term of this patent is extended or adjusted under 35 U.S.C. 154(b) by 0 days.

(21) Appl. No.: 16/754,432

(22) PCT Filed: Oct. 3, 2018

(86) PCT No.: PCT/US2018/054101
§ 371 (c)(1),
(2) Date: Apr. 8, 2020

(87) PCT Pub. No.: WO2019/089173
PCT Pub. Date: May 9, 2019

(65) Prior Publication Data
US 2020/0315928 A1 Oct. 8, 2020

Related U.S. Application Data

(60) Provisional application No. 62/579,366, filed on Oct. 31, 2017.

(51) Int. Cl.
| | | |
|---|---|---|
| *A61K 8/02* | (2006.01) | |
| *A61K 8/81* | (2006.01) | |
| *A61Q 1/02* | (2006.01) | |
| *A61Q 19/00* | (2006.01) | |
| *C09B 69/10* | (2006.01) | |

(52) U.S. Cl.
CPC ............ *A61K 8/0241* (2013.01); *A61K 8/817* (2013.01); *A61K 8/8152* (2013.01); *A61Q 1/02* (2013.01); *A61Q 19/00* (2013.01); *C09B 69/10* (2013.01); *A61K 2800/57* (2013.01); *A61K 2800/654* (2013.01)

(58) Field of Classification Search
CPC ...... C09B 69/10; C09B 69/106; A61K 8/0241
See application file for complete search history.

(56) References Cited

U.S. PATENT DOCUMENTS

| | | | |
|---|---|---|---|
| 4,314,808 A * | 2/1982 | Jacquet | .............. A61K 8/418 |
| | | | 8/405 |
| 4,486,523 A | 12/1984 | Hosfeld et al. | |
| 5,521,253 A | 5/1996 | Lee et al. | |
| 5,662,707 A | 9/1997 | Jinkerson | |
| 5,795,507 A | 8/1998 | Crews et al. | |
| 6,384,104 B1 | 5/2002 | Chang et al. | |
| 7,563,457 B2 | 7/2009 | Cha et al. | |
| 7,868,059 B2 | 1/2011 | Vasudevan et al. | |
| 8,535,392 B2 | 9/2013 | Hong et al. | |
| 9,717,798 B2 | 8/2017 | Haddad et al. | |
| 2005/0031558 A1 | 2/2005 | Elder et al. | |
| 2009/0025601 A1* | 1/2009 | Vasudevan | .......... C09B 67/0033 |
| | | | 106/31.65 |
| 2012/0041165 A1* | 2/2012 | Greinert | ................. D06P 1/006 |
| | | | 526/257 |
| 2015/0126680 A1 | 5/2015 | Farrand et al. | |
| 2017/0027834 A1 | 2/2017 | Batchelor et al. | |

FOREIGN PATENT DOCUMENTS

| | | | | |
|---|---|---|---|---|
| WO | 2015158467 | | 10/2015 | |
| WO | WO-2016096085 A1 * | | 6/2016 | ............ C09B 35/06 |
| WO | 2017027286 | | 2/2017 | |
| WO | WO-2017027286 A1 * | | 2/2017 | .......... A61K 8/0279 |

(Continued)

OTHER PUBLICATIONS

Carolin Fleischmann, Melanie Lievenbrück. and Helmut Ritter. "Polymers and Dyes: Developments and Applications." Polymers, vol. 7, 2015, pp. 717-746. (Year: 2015).*

Hari R. Maradiya, Vithal S. Patel. "Studies of Novel Monomeric and Polymeric Azo Disperse Dyes." Journal of Applied Polymer Science, vol. 84, 2002, pp. 1380-1389. (Year: 2002).*

Douglas R. Robello. "Linear Polymers for Nonlinear Optics. I. Polyacrylates Bearing Aminonitro-Stilbene and Azobenzene Dyes." Journal of Polymer Science: Part A: Polymer Chemistry, vol. 28, 1990, pp. 1-13. (Year: 1990).*

(Continued)

*Primary Examiner* — Isaac Shomer
(74) *Attorney, Agent, or Firm* — Thomas S. Deibert

(57) ABSTRACT

A multistage colored polymer particle is provided, having a core comprising polymerized units of a monoethylenically unsaturated carboxylic acid core monomer and a non-ionic ethylenically unsaturated core monomer; an inner shell comprising polymerized units of a non-ionic ethylenically unsaturated inner shell monomer; a monoethylenically unsaturated carboxylic acid inner shell monomer; optionally, an aliphatic inner shell monomer; and, optionally, a first polymerizable dye monomer; an outer shell comprising polymerized units of a non-ionic ethylenically unsaturated outer shell monomer; a monoethylenically unsaturated non-carboxylic acid outer shell monomer; optionally, a second polymerizable dye monomer; and, optionally, an aliphatic outer shell monomer; wherein the core, when dry, contains at least one void; and wherein the multistage colored polymer particle comprises polymerized units of polymerizable dye monomer. Skin care formulations comprising multistage colored polymer particles and methods of using same are also provided.

9 Claims, No Drawings

(56) References Cited

FOREIGN PATENT DOCUMENTS

| WO | 2017058404 | 4/2017 |
| WO | 2018144298 | 8/2018 |

OTHER PUBLICATIONS

Chudgar, "Dyes, Azo," Kirk-Othmer Encyclopedia of Chemical Technology, p. 1-81, John Wiley & Sons.
Koh, "Dyeing with Disperse Dyes," Textile Dyeing, 2011, p. 195-220, InTech.

\* cited by examiner

MULTISTAGE COLORED POLYMER PARTICLE AND SKIN CARE FORMULATIONS COMPRISING SAME

The present invention relates to a multistage colored polymer particle. In particular, the present invention relates to a multistage colored polymer particle, having a core comprising polymerized units of a monoethylenically unsaturated carboxylic acid core monomer and a non-ionic ethylenically unsaturated core monomer; an inner shell comprising polymerized units of a non-ionic ethylenically unsaturated inner shell monomer; a monoethylenically unsaturated carboxylic acid inner shell monomer; optionally, an aliphatic inner shell monomer; and, optionally, a first polymerizable dye monomer; an outer shell comprising polymerized units of a non-ionic ethylenically unsaturated outer shell monomer; a monoethylenically unsaturated non-carboxylic acid outer shell monomer; optionally, a second polymerizable dye monomer; and, optionally, an aliphatic outer shell monomer; wherein the core, when dry, contains at least one void; and wherein the multistage colored polymer particle comprises polymerized units of polymerizable dye monomer. The present invention also relates to skin care formulations comprising multistage colored polymer particles and methods of using same.

Skin care formulations of a various kinds have found widespread use among consumers. In particular, skin care formulations for cosmetic uses, such as, moisturizing lotions or creams that may be applied to the skin of a consumer to obtain benefits such as anti-aging, skin lightening and moisturizing, and for providing enhancing and improving optical and color benefits.

There is an increasing demand from consumers for skin care formulations that provide skin care benefits that include the capability to alter the overall appearance of the skin. In contrast to make-up compositions, the desire from consumers is for skin care formulations that enhance one's existing skin tones or result in a natural skin tone appearance.

Pigment particles may provide optical benefits for skin care formulations, however, they also tend to have the disadvantage that their presence can lead to an undesired poor tactile sensory property. Various small molecule colorants, such as dyes, present the disadvantage of being skin permeable, hence their use is highly regulated. Also, the coloring benefits imparted by both pigments and dyes lack resilience are typically easily removed from skin after application resulting in short-lived effects.

It would accordingly be desirable to provide skin care formulations having more longer lasting skin tone enhancing properties along with better tactile sensory properties.

An approach to providing such skin care formulations is disclosed by Gu et al. in WO 2017/027286. In WO 2017/027286 Gu et al. disclose personal care formulations containing voided latex particles comprising a core polymer and a shell polymer, and having a particle size of 400 to 1,500 nm, wherein the voided latex particles provide improved light scattering to compositions containing pigment grade inorganic metal oxide particles, as well as providing a long lasting whitening effect when applied to skin. Notwithstanding, the whitening effect provided by the voided latex particles taught in WO 2017/027286 can be perceived as unnatural by many consumers.

Accordingly, there remains a need for components and skin care formulations containing the same that provide skin care benefits such as skin lightening, evening skin tone and masking of skin blemishes.

The present invention provides a multistage colored polymer particle for use in a skin care formulation, comprising: (i) a core, wherein the core comprises, as polymerized units, 20 to 60 wt %, based on weight of the core, of a monoethylenically unsaturated carboxylic acid core monomer; and 40 to 80 wt %, based on weight of the core, of a non-ionic ethylenically unsaturated core monomer; (ii) an inner shell, wherein the inner shell comprises, as polymerized units, 90 to 99.9 wt %, based on weight of the inner shell, of a non-ionic ethylenically unsaturated inner shell monomer; 0.01 to 9.95 wt %, based on weight of the inner shell, a monoethylenically unsaturated carboxylic acid inner shell monomer; 0 to 9.99 wt %, based on weight of the inner shell, of an aliphatic inner shell monomer selected from the group consisting of allyl acrylate, allyl methacrylate and mixtures thereof; and 0 to 10 wt %, based on weight of the inner shell, of a first polymerizable dye monomer; (iii) an outer shell, wherein the outer shell comprises, as polymerized units, 15 to 99.5 wt %, based on weight of the outer shell, of a non-ionic ethylenically unsaturated outer shell monomer; 0.1 to 10 wt %, based on weight of the outer shell, of a monoethylenically unsaturated non-carboxylic acid outer shell monomer; 0 to 10 wt %, based on weight of the outer shell, of a second polymerizable dye monomer; and 0 to 70 wt %, based on weight of the outer shell, of an aliphatic outer shell monomer selected from the group consisting of allyl acrylate, allyl methacrylate and mixtures thereof; wherein the core, when dry, contains at least one void; wherein the first polymerizable dye monomer and the second polymerizable dye monomer are the same or different; and wherein the multistage colored polymer particle comprises, as polymerized units, 0.015 to 8 wt %, based on weight of the multistage colored polymer particle, of the first polymerizable dye monomer and the second polymerizable dye monomer combined.

The present invention provides a multistage colored polymer particle for use in a skin care formulation, comprising: (i) a core, wherein the core comprises, as polymerized units, 20 to 60 wt %, based on weight of the core, of a monoethylenically unsaturated carboxylic acid core monomer; and 40 to 80 wt %, based on weight of the core, of a non-ionic ethylenically unsaturated core monomer; (ii) an inner shell, wherein the inner shell comprises, as polymerized units, 90 to 99.9 wt %, based on weight of the inner shell, of a non-ionic ethylenically unsaturated inner shell monomer; 0.01 to 9.95 wt %, based on weight of the inner shell, a monoethylenically unsaturated carboxylic acid inner shell monomer; and 0 to 9.99 wt %, based on weight of the inner shell, of an aliphatic inner shell monomer selected from the group consisting of allyl acrylate, allyl methacrylate and mixtures thereof; (iii) an outer shell, wherein the outer shell comprises, as polymerized units, 15 to 99.5 wt %, based on weight of the outer shell, of a non-ionic ethylenically unsaturated outer shell monomer; 0.1 to 10 wt %, based on weight of the outer shell, of a monoethylenically unsaturated non-carboxylic acid outer shell monomer; 0.1 to 10 wt %, based on weight of the outer shell, of a polymerizable dye monomer; and 0 to 70 wt %, based on weight of the outer shell, of an aliphatic outer shell monomer selected from the group consisting of allyl acrylate, allyl methacrylate and mixtures thereof; wherein the core, when dry, contains at least one void.

The present invention provides a skin care formulation, comprising: a multistage colored polymer particle of the present invention; and a dermatologically acceptable carrier.

The present invention provides a method of treating a selected area of skin, comprising: providing a skin care formulation of the present invention; and applying the skin care formulation to a selected area of skin.

DETAILED DESCRIPTION

We have surprisingly found that the multistage colored polymer particles of the present invention facilitate skin care formulations that provide skin lightening, evening skin tone and masking blemishes while achieving a more natural skin tone. It has also been found that the multistage colored polymer particles of the present invention facilitate skin care formulations that can be tailored to suit individual skin tones and desired resulting appearances.

Unless otherwise indicated, ratios, percentages, parts, and the like are by weight.

The term "polymerized units" as used herein and in the appended claims refers to the remnant of the indicated monomer; thus a structural unit of ethyl acrylate is illustrated:

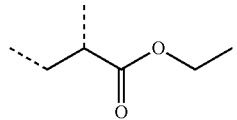

where the dotted lines represent the points of attachment to the polymer backbone.

The term "(meth)acrylic acid" as used herein and in the appended claims is intended to serve as a generic expression embracing both acrylic acid and methacrylic acid.

The term "(meth)acrylate" as used herein and in the appended claims is intended to serve as a generic expression embracing both acrylate and methacrylate.

The term "(meth)acrylamide" as used herein and in the appended claims is intended to serve as a generic expression embracing both acrylamide and methacrylamide.

The term "(meth)acryloxypropionic acid" as used herein and in the appended claims is intended to serve as a generic expression embracing both acryloxypropionic acid and methacryloxypropionic acid.

The term "dermatologically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the multistage colored polymer particle of the present invention, comprises: (i) (preferably, 1 to 25 wt % (more preferably, 2 to 12 wt %; still more preferably, 3 to 10 wt %; most preferably, 3.5 to 7.5 wt %), based on weight of the multistage colored polymer particle, of) a core, wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer; (ii) (preferably, 15 to 80 wt % (more preferably, 25 to 75 wt %; still more preferably, 30 to 60 wt %; most preferably, 40 to 50 wt %), based on weight of the multistage colored polymer particle of) an inner shell, wherein the inner shell comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; 0 to 9.99 wt % (preferably, 0 to 8 wt %; more preferably, 0 to 6 wt %; most preferably, 0 to 5 wt %), based on weight of the inner shell, of an aliphatic inner shell monomer selected from the group consisting of allyl acrylate, allyl methacrylate and mixtures thereof; and 0 to 10 wt % (preferably, 0 to 7.5 wt %; more preferably, 0 to 5 wt %; most preferably, 0 to 2 wt %), based on weight of the inner shell, of a first polymerizable dye monomer; (iii) (preferably, 15 to 80 wt % (more preferably, 25 to 75 wt %; still more preferably, 30 to 60 wt %; most preferably, 40 to 50 wt %), based on weight of the multistage colored polymer particle of) an outer shell, wherein the outer shell comprises, as polymerized units, 15 to 99.5 wt % (preferably, 20 to 99 wt %; more preferably, 30 to 98.5 wt %; most preferably, 90 to 97 wt %), based on weight of the outer shell, of a non-ionic ethylenically unsaturated outer shell monomer; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; 0 to 10 wt % (preferably, 0.25 to 7.5 wt %; more preferably, 0.5 to 5 wt %; most preferably, 0.75 to 2 wt %), based on weight of the outer shell, of a second polymerizable dye monomer; and 0 to 70 wt % (preferably, 0 to 80 wt %; more preferably, 0 to 65 wt %), based on weight of the outer shell, of an aliphatic outer shell monomer selected from the group consisting of allyl acrylate, allyl methacrylate and mixtures thereof; wherein the core, when dry, contains at least one void; wherein the first polymerizable dye monomer and the second polymerizable dye monomer are the same or different; and wherein the multistage colored polymer particle comprises, as polymerized units, 0.015 to 8 wt % (preferably, 0.04 to 6 wt %; more preferably, 0.07 to 4 wt %; most preferably, 0.1 to 1.6 wt %), based on weight of the multistage colored polymer particle, of the first polymerizable dye monomer and the second polymerizable dye monomer combined.

More preferably, the multistage colored polymer particle of the present invention, comprises: (i) (preferably, 1 to 25 wt % (more preferably, 2 to 12 wt %; still more preferably, 3 to 10 wt %; most preferably, 3.5 to 7.5 wt %), based on weight of the multistage colored polymer particle, of) a core, wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer; (ii) (preferably, 15 to 80 wt % (more preferably, 25 to 75 wt %; still more preferably, 30 to 60 wt %; most preferably, 40 to 50 wt %), based on weight of the multistage colored polymer particle of) an inner shell, wherein the inner shell comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0 to 9.99 wt % (preferably, 0 to 8 wt %; more preferably, 0 to 6 wt %; most preferably, 0 to 5 wt %), based on weight of the inner shell, of an aliphatic inner shell monomer selected from the group consisting of allyl acrylate, allyl methacrylate and mixtures thereof; (iii) (preferably, 15 to 80 wt % (more preferably, 25 to 75 wt %; still more preferably, 30 to 60 wt %; most preferably, 40 to 50 wt %), based on weight of the multistage colored polymer particle of) an outer shell, wherein the outer shell comprises, as polymerized units, 15 to 99.5 wt % (preferably, 20 to 99 wt %; more preferably, 30 to 98.5 wt %; most preferably, 90 to 97 wt %), based on weight of the outer shell, of a non-ionic ethylenically unsaturated outer shell monomer; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; 0.1 to 10 wt % (preferably, 0.25 to 7.5 wt %; more preferably, 0.5 to 5 wt %; most preferably, 0.75 to 2 wt %), based on weight of the outer shell, of a polymerizable dye monomer; and 0 to 70 wt % (preferably, 0 to 80 wt %; more preferably, 0 to 65 wt %), based on weight of the outer shell, of an aliphatic outer shell monomer selected from the group consisting of allyl acrylate, allyl methacrylate and mixtures thereof; and wherein the core, when dry, contains at least one void.

Preferably, the multistage colored polymer particle of the present invention, comprises a core, wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer. More preferably, the multistage colored polymer particle of the present invention, comprises 1 to 25 wt %, based on weight of the multistage colored polymer particle, of a core; wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer. Still more preferably, the multistage colored polymer particle of the present invention, comprises 2 to 12 wt %, based on weight of the multistage colored polymer particle, of a core; wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer. Yet still more preferably, the multistage colored polymer particle of the present invention, comprises 3 to 10 wt %, based on weight of the multistage colored polymer particle, of a core; wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer. Most preferably, the multistage colored polymer particle of the present invention, comprises 3.5 to 7.5 wt %, based on weight of the multistage colored polymer particle, of a core; wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt % more preferably, 55 to 65 wt %), based on weight of the core, of a non-ionic ethylenically unsaturated core monomer.

Preferably, the monoethylenically unsaturated carboxylic acid core monomer is selected from monoethylenically unsaturated monomers that contain at least one carboxylic acid group. More preferably, the monoethylenically unsaturated carboxylic acid core monomer is selected from the group consisting of (meth)acrylic acid, (meth)acryloxypropionic acid, itaconic acid, aconitic acid, maleic acid, maleic anhydride, fumaric acid, crotonic acid, citraconic acid, maleic anhydride, monomethyl maleate, monomethyl fumarate, monomethyl itaconate, and other derivatives such as corresponding anhydride, amides, and esters. Still more preferably, the monoethylenically unsaturated carboxylic acid core monomer is selected from the group consisting of acrylic acid, methacrylic acid and mixtures thereof. Yet still more preferably, the monoethylenically unsaturated carboxylic acid core monomer includes methacrylic acid. Most preferably, the monoethylenically unsaturated carboxylic acid core monomer is methacrylic acid.

Preferably, the non-ionic ethylenically unsaturated core monomer is selected from the group consisting of ethylene, vinyl acetate, vinyl chloride, vinylidene chloride acrylonitrile, (meth)acrylamide, methyl (meth)acrylate, ethyl (meth) acrylate, n-butyl (meth)acrylate, i-butyl (meth)acrylate, t-butyl (meth)acrylate, cyclo-hexyl (meth)acrylate, 2-ethylhexyl (meth)acrylate, lauryl (meth)acrylate, oleyl (meth) acrylate, palmityl (meth)acrylate, stearyl (meth)acrylate and mixtures thereof. More preferably, the non-ionic ethylenically unsaturated core monomer is selected from the group consisting of methyl methacrylate, butyl acrylate and mixtures thereof. Still more preferably, the non-ionic ethylenically unsaturated core monomer includes methyl methacrylate. Most preferably, the non-ionic ethylenically unsaturated core monomer is methyl methacrylate.

Preferably, the multistage colored polymer particle of the present invention, comprises an inner shell, wherein the inner shell comprises, as polymerized units, comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0 to 9.99 wt % (preferably, 0 to 8 wt %; more preferably, 0 to 6 wt %; most preferably, 0 to 5 wt %), based on weight of the inner shell, of an aliphatic inner shell monomer selected from the group consisting of allyl acrylate, allyl methacrylate and mixtures thereof. More preferably, the multistage colored polymer particle of the present invention, comprises 15 to 80 wt %, based on weight of the multistage colored polymer particle, of an inner shell, wherein the inner shell comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0 to 9.99 wt % (preferably, 0 to 8 wt %; more preferably, 0 to 6 wt %; most preferably, 0 to 5 wt %), based on weight of the inner shell, of an aliphatic inner shell monomer selected from the group consisting of allyl acrylate, allyl methacrylate and mixtures thereof. Still more preferably, the multistage colored polymer particle of the present invention, comprises 25 to 75 wt %, based on weight of the multistage colored polymer particle, of an inner shell, wherein the inner shell comprises, as polymerized units, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0 to 9.99 wt % (preferably, 0 to 8 wt %; more preferably, 0 to 6 wt %; most preferably, 0 to 5 wt %), based on weight of the inner shell, of an aliphatic inner shell monomer selected from the group consisting of allyl acrylate, allyl methacrylate and mixtures thereof. Yet still more preferably, the multistage colored polymer particle of the present invention, comprises 30 to 60 wt %, based on weight of the multistage colored polymer particle, of an inner shell, wherein the inner shell comprises, as polymerized units, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0 to 9.99 wt % (preferably, 0 to 8 wt %; more preferably, 0 to 6 wt %; most preferably, 0 to 5 wt %), based on weight of the inner shell, of an aliphatic inner shell monomer selected from the group consisting of allyl acrylate, allyl methacrylate and mixtures thereof. Most preferably, the multistage colored polymer particle of the present invention, comprises 40 to 50 wt %, based on weight of the multistage colored polymer particle, of an inner shell, wherein the inner shell comprises, as polymerized units, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0 to 9.99 wt % (preferably, 0 to 8 wt %; more preferably, 0 to 6 wt %; most preferably, 0 to 5 wt %), based on weight of the inner shell, of an aliphatic inner shell monomer selected from the group consisting of allyl acrylate, allyl methacrylate and mixtures thereof.

Preferably, the non-ionic ethylenically unsaturated inner shell monomer is selected from the group consisting of acrylonitrile, (meth)acrylamide, methyl (meth)acrylate, ethyl (meth)acrylate, n-butyl (meth)acrylate, i-butyl (meth)acrylate, t-butyl (meth)acrylate, cyclohexyl (meth)acrylate, 2-ethylhexyl (meth)acrylate, lauryl (meth)acrylate, oleyl (meth)acrylate, palmityl (meth)acrylate, stearyl (meth)acrylate, isobornyl (meth)acrylate, styrene, divinylbenzene and mixtures thereof. More preferably, the non-ionic ethylenically unsaturated inner shell monomer is selected from the group consisting of methyl acrylate, methyl methacrylate, ethyl acrylate, ethyl methacrylate, butyl acrylate, butyl methacrylate, isobutyl acrylate, isobutyl methacrylate, hydroxyethyl methacrylate, hydroxypropyl methacrylate, dimethylaminoethyl methacrylate, dimethylaminopropyl methacrylamide, styrene divinylbenzene and mixtures thereof. Still more preferably, the a non-ionic ethylenically unsaturated inner shell monomer is selected from the group consisting of at least one of butyl methacrylate, methyl methacrylate, styrene, divinylbenzene and mixtures thereof. Most preferably, the non-ionic ethylenically unsaturated inner shell monomer includes both styrene and divinylbenzene.

Preferably, the monoethylenically unsaturated carboxylic acid inner shell monomer is selected from monoethylenically unsaturated monomers that contain at least one carboxylic acid group. More preferably, the monoethylenically unsaturated carboxylic acid inner shell monomer is selected from the group consisting of (meth)acrylic acid, (meth)acryloxypropionic acid, itaconic acid, aconitic acid, maleic acid, fumaric acid, crotonic acid, citraconic acid, maleic anhydride monomethyl maleate, monomethyl fumarate, monomethyl itaconate, derivatives thereof (e.g., corresponding anhydride, amides, esters) and mixtures thereof. Still more preferably, the monoethylenically unsaturated carboxylic acid inner shell monomer is selected from the group consisting of acrylic acid, methacrylic acid and mixtures thereof. Yet still more preferably, the monoethylenically unsaturated carboxylic acid inner shell monomer includes methacrylic acid. Most preferably, the monoethylenically unsaturated carboxylic acid inner shell monomer is methacrylic acid.

Preferably, the aliphatic inner shell monomer is selected from the group consisting of allyl acrylate, allyl methacrylate and mixtures thereof. More preferably, the aliphatic inner shell monomer includes allyl methacrylate. Most preferably, the aliphatic inner shell monomer is allyl methacrylate.

Preferably, the multistage colored polymer particle of the present invention, comprises an inner shell, wherein the inner shell includes multiple inner shells. More preferably, the multistage colored polymer particle of the present invention, comprises an inner shell, wherein the inner shell includes: a first inner shell and a second inner shell. Most preferably, the multistage colored polymer particle of the present invention, comprises an inner shell, wherein the inner shell includes: (a) a first inner shell, wherein the first inner shell comprises, as polymerized units, 90 to 99.9 wt % (preferably, 92.5 to 99.5 wt %; more preferably, 95 to 99 wt %; most preferably, 96 to 98 wt %), based on weight of the first inner shell, of a non-ionic ethylenically unsaturated first inner shell monomer (preferably, wherein the non-ionic ethylenically unsaturated first inner shell monomer is selected from the group consisting of butyl methacrylate, methyl methacrylate and mixtures thereof; more preferably, wherein the non-ionic ethylenically unsaturated first inner shell monomer includes both butyl methacrylate and methyl methacrylate; most preferably, wherein the non-ionic ethylenically unsaturated first inner shell monomer is a mixture of butyl methacrylate and methyl methacrylate); and 0.1 to 10 wt % (preferably, 0.5 to 7.5 wt %; more preferably, 1 to 5 wt %; most preferably, 2 to 4 wt %), based on weight of the first inner shell, a monoethylenically unsaturated carboxylic acid first inner shell monomer (preferably, wherein the monoethylenically unsaturated carboxylic acid first inner shell monomer is selected from the group consisting of acrylic acid, methacrylic acid and mixtures thereof; more preferably, wherein the monoethylenically unsaturated carboxylic acid first inner shell monomer includes methacrylic acid; most preferably, wherein the monoethylenically unsaturated carboxylic acid first inner shell monomer is methacrylic acid); and (b) a second inner shell, wherein the second inner shell comprises, as polymerized units, 90 to 100 wt % (preferably, 92 to 100 wt %; more preferably, 94 to 100 wt %; most preferably, 95 to 100 wt %), based on weight of the second inner shell, of a non-ionic ethylenically unsaturated second inner shell monomer (preferably, wherein the non-ionic ethylenically unsaturated second inner shell monomer is selected from the group consisting of acrylonitrile, (meth)acrylamide, methyl (meth)acrylate, ethyl (meth)acrylate, n-butyl (meth)acrylate, i-butyl (meth)acrylate, t-butyl (meth)acrylate, cyclohexyl (meth)acrylate, 2-ethylhexyl (meth)acrylate, lauryl (meth)acrylate, oleyl (meth)acrylate, palmityl (meth)acrylate, stearyl (meth)acrylate, isobornyl (meth)acrylate, styrene, divinylbenzene and mixtures thereof; more preferable, wherein the non-ionic ethylenically unsaturated second inner shell monomer includes at least one of styrene and divinylbenzene; most preferably, wherein the non-ionic ethylenically unsaturated second inner shell monomer includes both styrene and divinylbenzene); and 0 to 10 wt % (preferably, 0 to 8 wt %; more preferably, 0 to 6 wt %), based on weight of the second inner shell, of an aliphatic second inner shell monomer selected from the group consisting of allyl acrylate, allyl methacrylate and mixtures thereof (preferably, wherein the aliphatic second inner shell monomer is allyl methacrylate).

Preferably, the multistage colored polymer particle of the present invention, comprises an outer shell, wherein the outer shell comprises, as polymerized units, 15 to 99.5 wt % (preferably, 20 to 99 wt %; more preferably, 30 to 98.5 wt %; most preferably, 90 to 97 wt %), based on weight of the outer shell, of a non-ionic ethylenically unsaturated outer shell monomer; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; 0.1 to 10 wt % (preferably, 0.25 to 7.5 wt %; more preferably, 0.5 to 5 wt %; most preferably, 0.75 to 2 wt %), based on weight of the outer shell, of a polymerizable dye monomer; and 0 to 70 wt % (preferably, 0 to 80 wt %; more preferably, 0 to 65 wt %), based on weight of the outer shell, of an aliphatic outer shell monomer selected from the group consisting of allyl acrylate, allyl methacrylate and mixtures thereof. More preferably, the multistage colored polymer particle of the present invention, comprises 15 to 80 wt %, based on weight of the multistage colored polymer particle, of an outer shell, wherein the outer shell comprises, as polymerized units, 15 to 99.5 wt % (preferably, 20 to 99 wt %; more preferably, 30 to 98.5 wt %; most preferably, 90 to 97 wt %), based on weight of the outer shell, of a non-ionic ethylenically unsaturated outer shell monomer; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; 0.1 to 10 wt % (preferably, 0.25 to 7.5 wt %; more preferably, 0.5 to 5 wt %; most preferably, 0.75 to 2 wt %), based on weight of the outer shell, of a polymerizable dye monomer; and 0 to 70 wt % (preferably, 0 to 80 wt %; more preferably, 0 to 65 wt %), based on weight of the outer shell, of an aliphatic outer shell monomer selected from the group consisting of allyl acrylate, allyl methacrylate and mixtures thereof. Still more preferably, the multistage colored polymer particle of the present invention, comprises 25 to 75 wt %, based on weight of the multistage colored polymer particle, of an outer shell, wherein the outer shell comprises, as polymerized units, 15 to 99.5 wt % (preferably, 20 to 99 wt %; more preferably, 30 to 98.5 wt %; most preferably, 90 to 97 wt %), based on weight of the outer shell, of a non-ionic ethylenically unsaturated outer shell monomer; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; 0.1 to 10 wt % (preferably, 0.25 to 7.5 wt %; more preferably, 0.5 to 5 wt %; most preferably, 0.75 to 2 wt %), based on weight of the outer shell, of a polymerizable dye monomer; and 0 to 70 wt % (preferably, 0 to 80 wt %; more preferably, 0 to 65 wt %), based on weight of the outer shell, of an aliphatic outer shell monomer selected from the group consisting of allyl acrylate, allyl methacrylate and mixtures thereof. Yet still more preferably, the multistage colored polymer particle of the present invention, comprises 30 to 60 wt %, based on weight of the multistage colored polymer particle, of an outer shell, wherein the outer shell comprises, as polymerized units, 15 to 99.5 wt % (preferably, 20 to 99 wt %; more preferably, 30 to 98.5 wt %; most preferably, 90 to 97 wt %), based on weight of the outer shell, of a non-ionic ethylenically unsaturated outer shell monomer; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; 0.1 to 10 wt % (preferably, 0.25 to 7.5 wt %; more preferably, 0.5 to 5 wt %; most preferably, 0.75 to 2 wt %), based on weight of the outer shell, of a polymerizable dye monomer; and 0 to 70 wt % (preferably, 0 to 80 wt %; more preferably, 0 to 65 wt %), based on weight of the outer shell, of an aliphatic outer shell monomer selected from the group consisting of allyl acrylate, allyl methacrylate and mixtures thereof. Most preferably, the multistage colored polymer particle of the present invention, comprises 40 to 50 wt %, based on weight of the multistage colored polymer particle, of an outer shell, wherein the outer shell comprises, as polymerized units, 15 to 99.5 wt % (preferably, 20 to 99 wt %; more preferably, 30 to 98.5 wt %; most preferably, 90 to 97 wt %), based on weight of the outer shell, of a non-ionic ethylenically unsaturated outer shell monomer; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; 0.1 to 10 wt % (preferably, 0.25 to 7.5 wt %; more preferably, 0.5 to 5 wt %; most preferably, 0.75 to 2 wt %), based on weight of the outer shell, of a polymerizable dye monomer; and 0 to 70 wt % (preferably, 0 to 80 wt %; more preferably, 0 to 65 wt %), based on weight of the outer shell, of an aliphatic outer shell monomer selected from the group consisting of allyl acrylate, allyl methacrylate and mixtures thereof.

Preferably, the non-ionic ethylenically unsaturated outer shell monomer is selected from the group consisting of acrylonitrile, (meth)acrylamide, methyl (meth)acrylate, ethyl (meth)acrylate, n-butyl (meth)acrylate, i-butyl (meth)acrylate, t-butyl (meth)acrylate, cyclohexyl (meth)acrylate, 2-ethylhexyl (meth)acrylate, lauryl (meth)acrylate, oleyl (meth)acrylate, palmityl (meth)acrylate, stearyl (meth)acrylate, isobornyl (meth)acrylate, styrene, divinylbenzene and mixtures thereof. More preferably, the non-ionic ethylenically unsaturated outer shell monomer is selected from the group consisting of methyl acrylate, methyl methacrylate, ethyl acrylate, ethyl methacrylate, butyl acrylate, butyl methacrylate, isobutyl acrylate, isobutyl methacrylate, hydroxyethyl methacrylate, hydroxypropyl methacrylate, dimethylaminoethyl methacrylate, dimethylaminopropyl methacrylamide, styrene and divinylbenzene and mixtures thereof. Still more preferably, the a non-ionic ethylenically unsaturated outer shell monomer includes at least one of methyl methacrylate, styrene and divinylbenzene. Most preferably, the non-ionic ethylenically unsaturated outer shell monomer includes both styrene and divinylbenzene.

Preferably, the monoethylenically unsaturated non-carboxylic acid outer shell monomer is selected from monoethylenically unsaturated monomers containing at least one non-carboxylic acid type acid group. More preferably, the monoethylenically unsaturated non-carboxylic acid outer shell monomer is selected from the group consisting of allyl sulfonic acid, allyl phosphonic acid, allyl oxybenzene sulfonic acid, 2-acrylamido-2-methylpropane sulfonic acid, 2-hydroxy-3-2-propenyloxy)propane sulfonic acid, 2-methyl-2-propene-1-sulfonic acid, 2-methacrylamido-2-methyl-1-propane sulfonic acid, 3-methacrylamido-2-hydroxy-1-propane sulfonic acid, 3-sulfopropyl acrylate, 3-sulfopropyl methacrylate, isopropenyl phosphonic acid, vinyl phosphonic acid, phosphoethyl methacrylate, styrene sulfonic acid, vinyl sulfonic acid, alkali metal salts thereof, ammonium salts thereof and mixtures thereof. Still more preferably, the monoethylenically unsaturated non-carboxylic acid outer shell monomer is selected from the group consisting of 2-acrylamido-2-methylpropane sulfonic acid, styrene sulfonic acid, sodium styrene sulfonate and mixtures thereof. Yet still more preferably, the monoethylenically unsaturated non-carboxylic acid outer shell monomer includes sodium styrene sulfonate. Most preferably, the monoethylenically unsaturated non-carboxylic acid outer shell monomer is sodium styrene sulfonate.

Preferably, the polymerizable dye monomer comprises at least one polymerizable moiety and at least one colorant moiety.

Preferably, the polymerizable moiety is selected from the group consisting of a polymerizable $C_{1-5}$ alkylacrylate moiety and a polymerizable acrylate moiety. More preferably, the polymerizable moiety is selected a polymerizable methacrylate moiety and a polymerizable acrylate moiety. Most preferably, the moiety is a polymerizable methacrylate moiety.

Preferably, the at least one colorant moiety is derived from a suitable dye. More preferably, the at least one colorant moiety is derived from a dye selected from the group consisting of food dyes, FD&C dyes, acid dyes, basic dyes, azo dyes, anthroquinone dye, naphthalimide dye, courmarin dye, xanthene dye, thioxanthene dye, naphtholactam dye, phthalocyanine dye, azlactone dye, methine dye, oxazine dye, thiazine dye, triphenylmethane dye, reactive dye, direct dye, vat dye, sulfur dye, disperse dye, mordant dye and fluorescent dye. Still more preferably, the at least one colorant moiety is derived from an azo dye. Yet still more preferable, the at least one colorant moiety is derived from a monoazo dye. Most preferably, the at least one colorant moiety is derived from a monoazo disperse dye.

Example dyes include Solvent Yellow 58, C.I. Reactive Yellow 2, C.I. Reactive Yellow 3, Disperse Yellow 3, Disperse Yellow 7, Disperse Yellow 13, Disperse Yellow, Pigment Red 100, C.I. Acid Red 440, C.I. Reactive Red 3, C.I. Reactive Red 13, C.I. Reactive Red 23, C.I. Reactive Red 24, C.I. Reactive Red 33, C.I. Reactive Red 43, C.I. Reactive Red 45, C.I. Reactive Red 120, C.I. Reactive Red 180, C.I. Reactive Red 194, C.I. Reactive Red 220, PROCION RED MX-5B, Disperse Red 17, Disperse Red 1, Lissamine™ rhodamine B, C.I. Reactive Violet 4, Reactive Blue 4, Reactint® Orange, Reactint® Green, Malachite Green.

Preferably, the polymerizable dye monomer is an acrylated chromophore of formula I

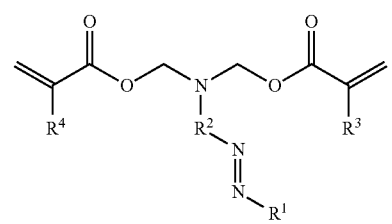

wherein $R^1$ is selected from the group consisting of an aryl group and a substituted aryl group (preferably, wherein $R^1$ is selected from the group consisting of a phenyl group, naphthyl group, a substituted phenyl group and a substituted naphthyl group; more preferably, wherein $R^1$ is selected from the group consisting of a phenyl group and a substituted phenyl group; most preferably, wherein $R^1$ is a phenyl group substituted with a —$NO_2$ group); wherein $R^2$ is selected from the group consisting of an aryl group and a substituted aryl group (preferably, wherein $R^2$ is selected from the group consisting of a phenyl group, naphthyl group, a substituted phenyl group and a substituted naphthyl group; more preferably, wherein $R^2$ is selected from the group consisting of a phenyl group and a substituted phenyl group; still more preferably, wherein $R^2$ is selected from the group consisting of a phenyl group substituted with at least one of a —$CH_3$ group and a —$N(H)C(O)CH_3$ group; most preferably, wherein $R^2$ is a phenyl group substituted with a —$CH_3$ group); and wherein $R^3$ and $R^4$ are independently selected from the group consisting of a —H and a —$C_{1-5}$ alkyl group (preferably, wherein $R^3$ and $R^4$ are independently selected from the group consisting of a —H and a —$C_{1-4}$ alkyl group; more preferably, wherein $R^3$ and $R^4$ are independently selected from the group consisting of a —H and a —$CH_3$ group; most preferably, wherein $R^3$ and $R^4$ are each a methyl group). More preferably, the polymerizable dye monomer is an acrylated chromophore of formula I wherein $R^1$ is a phenyl group substituted with a —$NO_2$ group; wherein $R^2$ is selected from the group consisting of a phenyl group substituted with at least one of a —$CH_3$ group and a —$N(H)C(O)CH_3$ group; and wherein $R^3$ and $R^4$ are each a methyl group. Most preferably, the polymerizable dye monomer is a Disperse Red 17 dimethacrylate of formula II

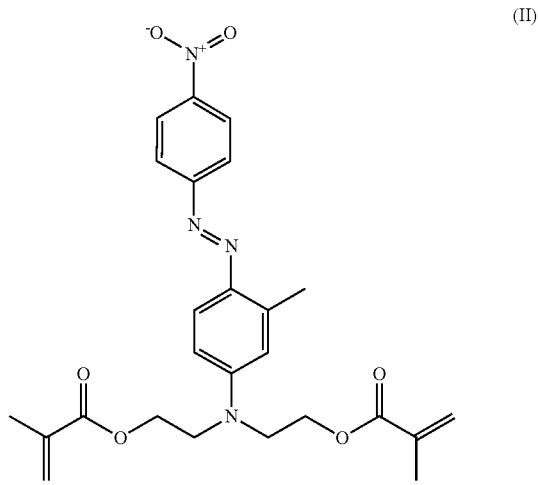

Preferably, the aliphatic outer shell monomer is selected from the group consisting of allyl acrylate, allyl methacrylate and mixtures thereof. More preferably, the aliphatic outer shell monomer includes allyl methacrylate. Most preferably, the aliphatic outer shell monomer is allyl methacrylate.

Preferably, the multistage colored polymer particle of the present invention, comprises an inner shell(s) and an outer shell, wherein the outer shell comprises at least 25 wt % of the combined weight of the inner shell(s) and the outer shell. More preferably, the multistage colored polymer particle of the present invention, comprises an inner shell(s) and an outer shell, wherein the outer shell comprises at least 35 wt % of the combined weight of the inner shell(s) and the outer shell. Most preferably, the multistage colored polymer particle of the present invention, comprises an inner shell(s) and an outer shell, wherein the outer shell comprises at least 45 wt % of the combined weight of the inner shell(s) and the outer shell.

Preferably, the multistage colored polymer particle of the present invention, comprises a core, wherein the core, when dry, contains at least one void. More preferably, the multistage colored polymer particle of the present invention, comprises a core, wherein the core, when dry, contains at least one void having a void fraction of 5 to 70 vol %, based on the volume occupied by the multistage colored polymer particle. Still more preferably, the multistage colored polymer particle of the present invention, comprises a core, wherein the core, when dry, contains at least one void having a void fraction of 10 to 60 vol %, based on the volume occupied by the multistage colored polymer particle. Yet still more preferably, the multistage colored polymer particle of the present invention, comprises a core, wherein the core, when dry, contains at least one void having a void fraction of 20 to 50 vol %, based on the volume occupied by the multistage colored polymer particle. Most preferably, the multistage colored polymer particle of the present invention, comprises a core, wherein the core, when dry, contains at least one void having a void fraction of 25 to 45 vol %, based on the volume occupied by the multistage colored polymer particle. The void fraction is determined by comparing the volume occupied by a plurality of the multistage colored polymer particles after compaction from a dilute dispersion in a centrifuge to the volume of non-voided multistage colored polymer particles having the same composition.

Preferably, the multistage colored polymer particle of the present invention, comprises an inner shell and an outer shell, wherein the $T_g$ (as measured by DSC) of the inner shell and the outer shell are high enough to support the at least one void contained in the core. More preferably, the multistage colored polymer particle of the present invention, comprises an inner shell and an outer shell, wherein the $T_g$ (as measured by DSC) of at least one of the inner shell and the outer shell is greater than 50° C. Still more preferably, the multistage colored polymer particle of the present invention, comprises an inner shell and an outer shell, wherein the $T_g$ (as measured by DSC) of at least one of the inner shell and the outer shell is greater than 60° C. Most preferably, the multistage colored polymer particle of the present invention, comprises an inner shell and an outer shell, wherein the $T_g$ (as measured by DSC) of at least one of the inner shell and the outer shell is greater than 70° C.

Preferably, the multistage colored polymer particles of the present invention have an average particle size, when dry, of 50 to 1,500 nm, as measured by a Brookhaven BI-90. More preferably, the multistage colored polymer particles of the present invention have an average particle size, when dry, of 100 to 1,000 nm, as measured by a Brookhaven BI-90. Still more preferably, the multistage colored polymer particles of the present invention have an average particle size, when dry, of 200 to 800 nm, as measured by a Brookhaven BI-90. Most preferably, the multistage colored polymer particles of the present invention have an average particle size, when dry, of 300 to 600 nm, as measured by a Brookhaven BI-90.

Preferably, the multistage colored polymer particle contains, as polymerized units, less than 5 wt %, based on weight of the multistage colored polymer particle, of total styrene monomer in the backbone chain of the core, the inner shell and the outer shell combined styrene. More preferable, the multistage colored polymer particle contains, as polymerized units, less than 2.5 wt %, based on weight of the multistage colored polymer particle, of total styrene monomer in the backbone chain of the core, the inner shell and the outer shell combined styrene. Yet more preferably, the multistage colored polymer particle is substantially free (i.e., less than 0.001 wt % (preferably, less than 0.0001 wt %; most preferably, less than 1 part per million by weight,) based on weight of the multistage colored polymer particle,) of polymerized units of styrene monomer in the backbone chain of the core, the inner shell and the outer shell combined. Most preferably, the multistage colored polymer particle is free (i.e., contains 0 wt %, based on weight of the multistage colored polymer particle,) of polymerized units of styrene monomer in the backbone chain of the core, the inner shell and the outer shell combined.

Preferably, the multistage colored polymer particles are prepared using conventional polymerization techniques. More preferably, the multistage colored polymer particles are prepared using a single polymerization step or a sequence of polymerization steps. Still more preferably, the multistage colored polymer particles are prepared via a sequential emulsion polymerization process. Preferably, the monomers used in the emulsion polymerization of the shell(s) comprise one or more non-ionic ethylenically unsaturated monomer(s).

Aqueous emulsion polymerization processes are typically conducted in an aqueous reaction mixture, which contains at least one monomer and various synthesis adjuvants, such as free radical sources, buffers, chain transfer agents and reductants in an aqueous reaction medium. The aqueous reaction medium is the continuous fluid phase of the aqueous reaction mixture and contains more than 50 weight % water and optionally one or more water miscible solvents, based on the weight of the aqueous reaction medium. Suitable water miscible solvents include, for example, methanol, ethanol, propanol, acetone, ethylene glycol ethyl ethers, propylene glycol propyl ethers, and diacetone alcohol.

Preferably, in the process of manufacturing the multistage colored polymer particles, the void is formed by swelling the core with a swelling agent containing one or more volatile components. The swelling agent permeates the shell(s) to swell the core. The volatile components of the swelling agent can then be removed by drying the multistage colored polymer particles, causing a void to be formed within the core. Preferably, the swelling agent includes an aqueous base, such as, for example ammonia, ammonium hydroxide, alkali metal hydroxides (e.g., sodium hydroxide) and volatile amines (e.g., trimethylamine, triethylamine).

Preferably, the multistage colored polymer particles of the present invention are dried before incorporation into a skin care formulation of the present invention. More preferably, the multistage colored polymer particles of the present invention are spray dried before incorporation into the skin care formulation of the present invention using well known processing techniques.

Preferably, the skin care formulation of the present invention, comprises: a multistage colored polymer particle according to the present invention; and a dermatologically acceptable carrier. More preferably, the skin care formulation of the present invention, comprises 0.5 to 20 wt % (preferably, 1 to 15 wt %; more preferably, 1.5 to 10 wt %; most preferably, 2 to 6 wt %) of a multistage colored polymer particle according to the present invention. Still more preferably, the skin care formulation of the present invention, comprises 0.5 to 20 wt % (preferably, 1 to 15 wt %; more preferably, 1.5 to 10 wt %; most preferably, 2 to 5 wt %) of a multistage colored polymer particle according to the present invention; wherein the multistage colored polymer particle comprises, comprises: (i) a core, wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer; (ii) an inner shell, wherein the inner shell comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0 to 9.99 wt % (preferably, 0 to 8 wt %; more preferably, 0 to 6 wt %; most preferably, 0 to 5 wt %), based on weight of the inner shell, of an aliphatic inner shell monomer selected from the group consisting of allyl acrylate, allyl methacrylate and mixtures thereof; (iii) an outer shell, wherein the outer shell comprises, as polymerized units, 15 to 99.5 wt % (preferably, 20 to 99 wt %; more preferably, 30 to 98.5 wt %; most preferably, 90 to 97 wt %), based on weight of the outer shell, of a non-ionic ethylenically unsaturated outer shell monomer; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; 0.1 to 10 wt % (preferably, 0.25 to 7.5 wt %; more preferably, 0.5 to 5 wt %; most preferably, 0.75 to 2 wt %), based on weight of the outer shell, of a polymerizable dye monomer; and 0 to 70 wt % (preferably, 0 to 80 wt %; more preferably, 0 to 65 wt %), based on weight of the outer shell, of an aliphatic outer shell monomer selected from the group consisting of allyl acrylate, allyl methacrylate and mixtures thereof; wherein the core, when dry, contains at least one void; and wherein the multistage colored polymer particle has an average particle size, when dry, of 50 to 1,500 nm (preferably, 100 to 1,000 nm; more preferably, 200 to 800 nm; most preferably, 300 to 600). Most preferably, the skin care formulation of the present invention, comprises 0.5 to 20 wt % (preferably, 1 to 15 wt %; more preferably, 1.5 to 10 wt %; most preferably, 2 to 5 wt %) of a multistage colored polymer particle according to the present invention; wherein the multistage colored polymer particle comprises, comprises: (i) 1 to 25 wt % (more preferably, 2 to 12 wt %; still more preferably, 3 to 10 wt %; most preferably, 3.5 to 7.5 wt %), based on weight of the multistage colored polymer particle, of a core, wherein the core comprises, as polymerized units, 20 to 60 wt % (preferably, 30 to 50 wt %; more preferably, 35 to 45 wt %), based on weight of the core, of a monoethylenically unsaturated carboxylic acid core monomer; and 40 to 80 wt % (preferably, 50 to 70 wt %; more preferably, 55 to 65 wt %), based on weight of the core, of a non-ionic ethylenically unsaturated core monomer; (ii) 15 to 80 wt % (more preferably, 25 to 75 wt %; still more preferably, 30 to 60 wt %; most preferably, 40 to 50 wt %), based on weight of the multistage colored polymer particle of an inner shell, wherein the inner shell comprises, as polymerized units, 90 to 99.9 wt % (preferably, 92.5 to 99.5 wt %; more preferably, 95 to 99 wt %; most preferably, 96 to 98 wt %), based on weight of the inner shell, of a non-ionic ethylenically unsaturated inner shell monomer; 0.01 to 9.95 wt % (preferably, 0.05 to 7.5 wt %; more preferably, 0.1 to 5 wt %; most preferably, 0.2 to 4 wt %), based on weight of the inner shell, a monoethylenically unsaturated carboxylic acid inner shell monomer; and 0 to 9.99 wt % (preferably, 0 to 8 wt %; more preferably, 0 to 6 wt %; most preferably, 0 to 5 wt %), based on weight of the inner shell, of an aliphatic inner shell monomer selected from the group consisting of allyl acrylate, allyl methacrylate and mixtures thereof; (iii) 15 to 80 wt % (more preferably, 25 to 75 wt %; still more preferably, 30 to 60 wt %; most preferably, 40 to 50 wt %), based on weight of the multistage colored polymer particle of an outer shell, wherein the outer shell comprises, as polymerized units, 15 to 99.5 wt % (preferably, 20 to 99 wt %; more preferably, 30 to 98.5 wt %; most preferably, 90 to 97 wt %), based on weight of the outer shell, of a non-ionic ethylenically unsaturated outer shell monomer; 0.1 to 10 wt % (preferably, 0.5 to 7.5 wt %; more preferably, 1 to 5 wt %; most preferably, 2 to 3 wt %), based on weight of the outer shell, of a monoethylenically unsaturated non-carboxylic acid outer shell monomer; 0.1 to 10 wt % (preferably, 0.25 to 7.5 wt %; more preferably, 0.5 to 5 wt %; most preferably, 0.75 to 2 wt %), based on weight of the outer shell, of a polymerizable dye monomer; and 0 to 70 wt % (preferably, 0 to 80 wt %; more preferably, 0 to 65 wt %), based on weight of the outer shell, of an aliphatic outer shell monomer selected from the group consisting of allyl acrylate, allyl methacrylate and mixtures thereof; wherein the core, when dry, contains at least one void; and wherein the multistage colored polymer particle has an average particle size, when dry, of 50 to 1,500 nm (preferably, 100 to 1,000 nm; more preferably, 200 to 800 nm; most preferably, 300 to 600).

Preferably, the skin care formulation of the present invention, comprises a dermatologically acceptable carrier. More preferably, the skin care formulation of the present invention, comprises 30 to 99.99 wt % (preferably, 35 to 92 wt %; more preferably, 40 to 80 wt %) of a dermatologically acceptable carrier.

Preferably, the dermatologically acceptable carrier does not cause significant irritation to the skin and does not negate the activity and properties of any active agents included in the skin care formulation. Examples of dermatologically acceptable carriers include, water (such as deionized or distilled water), emulsions (such as oil-in-water or water-in-oil emulsions), alcohol (such as a $C_{1-4}$ straight or branched chain alcohols (e.g., methyl alcohol, ethyl alcohol, propyl alcohol, isopropyl alcohol, butyl alcohol)), glycol (such as ethylene glycol, propylene glycol, butylene glycol, pentylene glycol, hexylene glycol, dipropylene glycol, ethoxydiglycol), glycerin, acetone, methyl acetate, butyl cellosolve, creams, aqueous solutions, oils, ointments, pastes, gels, lotions, milks, foams, suspensions, powders and mixtures thereof.

Preferably, the skin care formulation of the present invention, further comprises an optional additive. More preferably, the skin care formulation of the present invention, further comprises an optional additive, wherein the optional additive is selected from the group consisting of film forming agent, water proofing agents, emollients, preservatives, antioxidants, fragrances, humectants, rheology modifiers, thickening agents, suspending agents, sequestering agents, aesthetic modifiers, Vitamins, skin protectants, oils, emulsifiers, surfactants, pearlizers, consistency factors, thickeners, super fatting agents, stabilizers, polymers, silicone compounds, fats, waxes, lectins, phospholipids, UV absorbers, UV boosters, UV blockers, moisturizers, medicaments and mixtures thereof. Most preferably, the suncare formulation of the present invention, further comprises an optional additive, wherein the optional additive includes a film forming agent.

Optionally, the skin care formulation of the present invention, further comprises at least two different multistage colored polymer particles of the present invention. More preferably, the skin care formulation of the present invention, further comprises at least two different multistage colored polymer particles of the present invention; wherein the at least two different multistage colored polymer particles include a red multistage colored polymer particle and a yellow multistage colored polymer particle.

Preferably, when the skin care formulation of the present invention, further comprises at least two different multistage colored polymer particles of the present invention; the skin care formulation is provided as a two part skin care formulation; wherein each part contains a multistage colored polymer particle according to the present invention; wherein the multistage colored polymer particle contained in each part is different (preferably, wherein a red multistage colored polymer particle is included in one part and a yellow multistage colored polymer particle is included in the second part); such that the two parts can be blended in desired ratios to obtain a natural, textured tone effect in a customizable fashion to satisfy the individualized tastes of each user to accommodate his or her unique skin tone.

Preferably, the skin care formulation of the present invention, further comprises a medicament. More preferably, the skin care formulation of the present invention, further comprises a medicament; wherein the dermatologically acceptable carrier preferably includes at least one of water and a $C_{1-4}$ straight or branch chain alcohol; and wherein the multistage colored polymer particle does not react directly or indirectly with the medicament.

Preferably, the skin care formulation of the present invention, further comprises a medicament; wherein the medicament comprises an antimicrobial agent. More preferably, the skin care formulation of the present invention, further comprises a medicament; wherein the medicament comprises an antimicrobial agent; and wherein, when the skin care formulation is contacted for a period of time with an area of a surface having a number of cultivable microorganisms present thereon, the concentration of the antimicrobial agent in the skin care formulation is sufficient to reduce the number of cultivable microorganisms on the area of the surface. Most preferably, the skin care formulation of the present invention, further comprises a medicament; wherein the medicament comprises an antimicrobial agent; wherein the antimicrobial agent comprises at least one of chemical antiseptic compound and an antiseptic alcohol; and wherein, when the skin care formulation is contacted for a period of time with an area of a surface having a number of cultivable microorganisms present thereon, the concentration of the antimicrobial agent in the skin care formulation is sufficient to reduce the number of cultivable microorganisms on the area of the surface. Preferably, the chemical antiseptic compound is a cationic antiseptic compound. Preferably, the cationic antiseptic compound is selected from the group consisting of chlorhexidine, polyhexamethylene biguanide, octenidine, salts thereof, and mixtures thereof.

Preferably, the medicament is a substance capable of eliciting a desired and clinically therapeutic response (e.g., at least one of a local or systemic biological response) when the skin care composition of the present invention containing the substance is applied to skin. Preferably, the medicament includes an antimicrobial agent. Preferably, the medicament includes an antimicrobial agent selected from the group consisting of at least one of an antiseptic agent, an antibiotic agent, an analgesic agent, an anesthetic agent and an enzymatic agent.

Antimicrobial agents include biquanides (e.g., chlorohexidine salts); phenolic antiseptics (e.g., parachlorometaxylenol, triclosan, hexachlorophene); fatty acid monoesters of glycerin and propylene glycol (e.g., glycerol monolaurate, glycerol monocaprylate, glycerol monocaprate, propylene glycol monolaurate, propylene glycol monocaprylate, propylene glycol monocaprate); hydrogen peroxide; silver, silver salts and mixtures thereof.

Antiseptic agents include parabens; formaldehyde donors; 2-phenoxyethanol; benzyl alcohol; acids (e.g., benzoic acid, sorbic acid, citric acid, and salts thereof); quaternary ammonium surfactants (e.g., benzalkonium chloride).

Antibiotic agents include neomycin sulfate, bacitracin, mupirocin, polymyxin, gentamycin, nitrofurantoin, sulfamethoxazole trymethoprim, rifampin, tetracycline, lysostaphin and mixtures thereof.

Analgesic agents include aspirin, methyl salicylate, camphor, menthol, a lower alcohol (ethanol, isopropanol) and mixtures thereof.

Anesthetic agents include lidocaine, benzocaine, priolocane, dexamethasone, dexamethasone sodium phosphate, dexamethasone acetate and mixtures thereof.

Preferably, the method of treating a selected area of skin (preferably, mammalian skin; more preferably, human skin) of the present invention, comprises providing a skin care formulation of the present invention; and applying the skin care formulation to a selected area of skin. More preferably, the method of treating skin of the present invention, comprises providing a skin care formulation of the present invention; and applying the skin care formulation to skin (preferably, mammalian skin; more preferably, human skin); wherein the skin care formulation delivers a skin care benefit when applied to skin. Still more preferable, the method of treating skin of the present invention, comprises providing a skin care formulation of the present invention; and applying the skin care formulation to human skin; wherein the skin care formulation delivers a skin care benefit when applied to skin; and wherein the skin care benefit includes at least one of providing a natural tone to the selected area of skin, enhancing the natural tone of the selected area of skin, providing a pinkish appearance to the selected area of skin, and enhancing the pinkish appearance of the selected area of skin.

Preferably, the method of treating a selected area of skin (preferably, mammalian skin; more preferably, human skin) of the present invention is specifically a method of preparing the selected area of skin as a site for a surgical procedure (preferably, a percutaneous procedure) of the present invention, comprises: providing a skin care formulation of the present invention comprising a multistage colored polymer particle; a medicament, wherein the medicament comprises an antimicrobial agent (preferably, wherein the antimicrobial agent is present in the skin care formulation at a concentration of at least 0.25 wt % of the skin care formulation); and a dermatologically acceptable carrier, wherein the dermatologically acceptable carrier includes a mixture of a $C_{1-4}$ straight or branched chain alcohol and water (preferably, a mixture of water and at least one of methyl alcohol, ethyl alcohol, propyl alcohol, isopropyl alcohol, butyl alcohol; more preferably, a mixture of water and at least one of methyl alcohol, ethyl alcohol and isopropyl alcohol); and wherein the multistage colored polymer particle does not react directly or indirectly with the antimicrobial agent; applying the skin care formulation to a selected area of skin (preferably, mammalian skin; more preferably, human skin); wherein the selected area of skin has a number of cultivable microorganisms present thereon; wherein, when the skin care formulation is applied for a period of time to the selected area of skin, the concentration of the antimicrobial agent in the skin care formulation is sufficient to reduce the number of cultivable microorganisms on the selected area of skin; wherein application of the skin care formulation to the selected area of skin results in a reduction in the number of cultivable microorganisms present thereon; and wherein the multistage colored polymer particle in the skin care formulation imparts a color to the selected area of skin where the skin care formulation was applied; and verifying the selected area of skin to which the skin care formulation was applied by observing for the color imparted by the multistage colored polymer particle.

Some embodiments of the present invention will now be described in detail in the following Examples.

EXAMPLE 1

Preparation of Polymerizable Dye Monomer

A polymerizable dye monomer (Disperse Red 17 Dimethacrylate) according to the formula

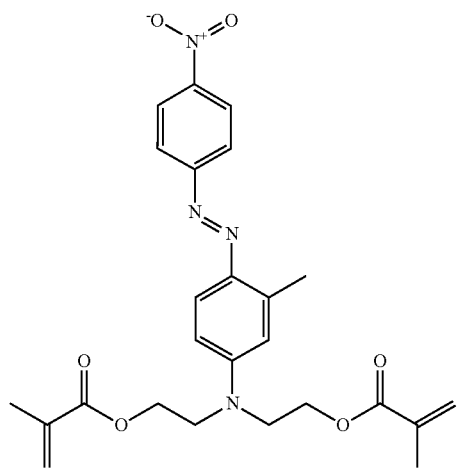

was prepared in a 500 mL, 3-neck round bottom flask equipped with a water condenser, magnetic stirrer, a heating plate with water bath, and a nitrogen inlet/outlet. To the flask was added Disperse Red 17 (20.66 g), triethylamine (13.35 g), 4-methoxyphenol (MEHQ, 20 mg) and dichloromethane (360 mL). The flask contents were then stirred for dissolution at room temperature followed by the slow addition to the flask contents of methacrylic anhydride (20.35 g). The flask contents were then heated slowly to 40° C., with mild refluxing for one hour. Water was then added to the flask contents. Then a saturated sodium chloride solution (50 mL) was added to the flask contents with stirring. Following phase separation of the flask contents, the organic layer was isolated and washed 3 times with deionized water. The polymerizable dye monomer (Disperse Red 17 dimethacrylate, 28 g) was then obtained by removing the organic solvent from the isolated and washed organic layer in an evaporator under vacuum.

COMPARATIVE EXAMPLE C1 and EXAMPLE 2

Multistage Polymer Particle

A multistage polymer particle was prepared in Comparative Example C1 and Example 2 comprising a core, a first inner shell, a second inner shell and an outer shell in the weight percent noted in TABLE 1. The multistage polymer particle in Comparative Example C1 and Example 2 both comprised a composition for the core, the first inner shell and the second inner shell, as described in TABLE 2. The composition of the outer shell of the multistage polymer particle in Comparative Example C1 and Example 2 were as described in TABLE 3.

TABLE 1

| | (wt %) | | | |
|---|---|---|---|---|
| Example | Core | $1^{st}$ inner shell | $2^{nd}$ inner shell | Outer shell |
| Comparative Example C1 | 4.7 | 22.1 | 26.8 | 46.4 |
| Example 2 | 4.65 | 21.85 | 26.51 | 45.89 |

TABLE 2

| Component | Polymerized units of (wt %) | | | | |
|---|---|---|---|---|---|
| Composition | MMA | MAA | BMA | DVB | Styrene |
| core | 60.0 | 40.0 | — | — | — |
| $1^{st}$ inner shell | 88.5 | 3.0 | 8.5 | — | — |
| $2^{nd}$ inner shell | — | — | — | 5.1 | 94.9 |

MMA = methyl methacrylate
MAA = methacrylic acid
BMA = butyl methacrylate
ALMA = allyl methacrylate
DVB = divinyl benzene

TABLE 3

| Outer Shell | Polymerized units of (wt %) | | | |
|---|---|---|---|---|
| Composition | Styrene | DVB | SSS | Dye |
| Comparative Example C1 | 46.2 | 51.1 | 2.7 | — |
| Example 2 | 45.6 | 50.4 | 2.7 | 1.3 |

DVB = divinyl benzene
SSS = sodium styrene sulfonate
Dye = polymerizable dye monomer prepared according to Example 1

COMPARATIVE EXAMPLE C1

Preparation Multistage Polymer Particles

Multistage polymer particles of Comparative Example 1 were prepared by adding 875.3 g of deionized water to a 3 liter, 4 neck round bottom flask equipped with an overhead stirrer, a thermocouple, a heating mantle, an adapter inlet, a Claisen head fitted with a water condenser and a nitrogen inlet. The flask contents were then heated to 84° C. under nitrogen. Then a solution of deionized water (15.5 g), acetic acid (0.30 g) and sodium persulfate (1.70 g) was added to the flask. Then an aqueous dispersion of 31 wt % solids poly (60 wt % MMA/40 wt % MAA) acrylic seed (core) polymer, having an average particle diameter of 133 nm, was added to the flask. While maintaining the temperature of the flask contents at 82° C., a monomer emulsion containing deionized water (71.5 g), a 23% aqueous solution of sodium dodecylbenzenesulfonate (SDBS)(2.1 g), MMA (91.6 g), BMA (8.9 g) and MAA (3.1 g) was metered into the flask contents over a period of 90 minutes followed by a deionized water rinse of the transfer lines. Next a solution of sodium persulfate (0.65 g) in deionized water (32.8 g) was added to the flask contents over a period of 90 minutes. The temperature set point for the flask contents was then raised to 90° C., concurrent with the transfer to the flask contents of a second monomer emulsion containing deionized water (48.3 g), a 23% aqueous solution of SDBS (0.35 g), styrene (120.5 g), DVB (6.45 g) and linseed oil fatty acid (0.70 g) over a period of 30 minutes, minutes followed by a deionized water rinse of the transfer lines. Then, a 28% aqueous ammonium hydroxide solution (8.1 g) was added to the flask contents. The flask contents were held for 10 minutes, before adding a third monomer emulsion containing deionized water (183.0 g), a 23% aqueous solution of SDBS (4.77 g), styrene (104.2 g), DVB (115.25 g), sodium styrene sulfonate (6.10 g) and linseed oil (1.10 g) to the flask contents at 91° C. over a period of 30 minutes; followed by a deionized water rinse of the transfer lines. Then (5.8 g) of an aqueous solution containing $FeSO_4 \cdot 7H_2O$ (0.10 g) and versene (0.10 g) was added to the contents of the flask. Then a solution of t-butylhydrogen peroxide (70%)(5.1 g) in deionized water (19.0 g) and a solution of isoascorbic acid (19.0 g) in deionized water (19.0 g) were concurrently added to the flask contents over 60 minutes. Then the flask was removed from the heating source and the flask contents were allowed to cool to room temperature and then filtered to provide the product multistage polymer particles.

EXAMPLE 2

Preparation of Multistage Colored Polymer Particles

The multistage colored polymer particles of Example 2 were prepared using the same process as described above for Comparative Example 1, with appropriate change in monomer amounts for the outer shell as recited in TABLE 3. The multistage colored polymer particles obtained were then washed by adding tetrahydrofuran (THF, 120 mL) to the product multistage colored polymer particles (30 g) and stirring for 3 hours. The solution was then centrifuged at 30 k rpm for a half hour with a Beckman L-80 ultracentrifuge using Type 70 Ti rotor and the supernatant was decanted. The spin down sample was then re-dispersed in THF (120 mL) and the process was repeated five times and air drying the final spin-down product sample for further characterization and application testing.

Multistage Polymer Particle Characterization

The average particle size of the multistage polymer particles in the latex of Comparative Example C1 was measured at 350 nm using a Brookhaven BI-90 particle size analyzer available from Brookhaven Instruments Corporation.

The percent void fraction for the multistage polymer particles in the latex of Comparative Example C1 was determined by taking a 10 wt % dispersion of the multistage polymer particles in propylene glycol, which was then mixed and poured into a weight-per-gallon cup which was capped and weighed. A 10 wt % water blank was also measured, and the difference in the weight was used to calculate the density of the sample, from which the percent void fraction was calculated to be 25 percent.

The average particle size of the multistage colored polymer particles prepared according to Example 2 was observed to be 372±106 nm using an FEI Nova NanoSEM electron microscope operating in transmission scanning mode. The average diameter of the void contained in the multistage colored polymer particles prepared according to Example 2 was observed to be 220±72 nm using the same technique.

COMPARATIVE EXAMPLES FB1 and FC1 and EXAMPLE F1

Formulations

Skin care formulations were prepared in each of Comparative Examples FB1 and FC1 and Example F1 having the component formulation noted in TABLE 4.

TABLE 4

| | Parts by weight (pbW) | | |
|---|---|---|---|
| Ingredient INCI name | FB1 | FC1 | F1 |
| Water | 84.15 | 79.15 | 79.15 |
| Xanthan Gum[1] | 0.30 | 0.30 | 0.3 |
| Disodium EDTA | 0.05 | 0.05 | 0.05 |
| Glycerin | 2.00 | 2.00 | 2.00 |
| Glyceryl Stearate[2] | 2.00 | 2.00 | 2.00 |
| Cetearyl Alcohol, Ceteareth-20[3] | 2.00 | 2.00 | 2.00 |
| Caprylic/Capric Triglyceride[4] | 5.00 | 5.00 | 5.00 |
| Dimethicone[5] | 2.00 | 2.00 | 2.00 |
| Product Comparative Example C1 | — | 5.00 | — |
| Product Example 2 | — | — | 5.00 |
| PEG-150/Decyl Alcohol/SMDI Copolymer[6] | 2.00 | 2.00 | 2.00 |
| Phenoxyethanol, isopropylparaben, isobutylparaben, butylparaben[7] | 0.50 | 0.50 | 0.50 |

[1]Keltrol CG-T xanthan gum available from CP Kelco
[2]Rita GMS glyceryl stearate available from Rita Corp.
[3]Procol CS-20-D cetearyl alcohol available from Protameen Chemicals
[4]Rita CCT caprylic/capric triglyceride available from Rita Corp.
[5]Xiameter ® PMX-200 100 cst available from The Dow Chemical Company
[6]Aculyn ™ 44 copolymer available from The Dow Chemical Company
[7]Liquapar ™ PE broad spectrum antimicrobial system available from Ashland

Hiding Test

The skin care formulations according to Comparative Examples FB1 and FC1 and Example F1 were evaluated for hiding to measure the contrast ratio for the respective skin care formulations. A film of each of the skin care formulations was drawn down on a black/white drawdown card. The purpose of this test is to facilitate an evaluation of the hiding power or opacity of the skin care formulations, which, in terms of skin care applications, relates to the ability of a given skin care formulation to mask skin defects and skin imperfections.

The drawdown film of each skin care formulation was prepared on a Leneta Form 2A black/white drawdown card using a BYK 3 MIL wet film applicator. The drawdown films were then allowed to air dry in ambient conditions for at least 12 hours. The reflectance of each drawdown film was then measured on both black card and white card using NOVO-SHADE Duo Reflectometer. The contrast ratio was then calculated according to the following equation:

CR=RBC/RWC wherein CR is the contrast ratio, RBC is the reflectance measured from the black card and RWC is the reflectance measured from the white card. The results are provided in TABLE 5.

TABLE 5

| Material | Reflectance Black Card (RBC) | Reflectance White Card (RWC) | Contrast Ratio (CR) |
|---|---|---|---|
| Blank Card | 0.3 | 80.5 | 0.00 |
| Comparative FB1 | 0.9 | 81.3 | 0.01 |
| Comparative FC1 | 38.0 | 83.2 | 0.46 |
| Example F1 | 39.1 | 72.8 | 0.54 |

COMPARATIVE EXAMPLES FB2 and FC2 and EXAMPLES F2-3

Formulations

Skin care formulations were prepared in each of Comparative Examples FB2 and FC2 and Examples F2-3 having the component formulation noted in TABLE 6.

TABLE 6

| Ingredient INCI name | Parts by weight (pbW) | | | |
|---|---|---|---|---|
| | FB2 | FC2 | F2 | F3 |
| Water | 79.15 | 74.15 | 74.15 | 74.15 |
| Xanthan Gum[1] | 0.30 | 0.30 | 0.30 | 0.30 |
| Disodium EDTA | 0.05 | 0.05 | 0.05 | 0.05 |
| Glycerin | 3.00 | 3.00 | 3.00 | 3.00 |
| Glyceryl Stearate[2] | 3.00 | 3.00 | 3.00 | 3.00 |
| Cetearyl Alcohol, Cetereth-20[3] | 3.00 | 3.00 | 3.00 | 3.00 |
| Caprylic/Capric Triglyceride[4] | 8.00 | 8.00 | 8.00 | 8.00 |
| Product Comparative Example C1 | — | 5.00 | — | 2.5 |
| Product Example 2 | — | — | 5.00 | 2.5 |
| PEG-150/Decyl Alcohol/SMDI Copolymer[5] | 3.00 | 3.00 | 3.00 | 3.00 |
| Phenoxyethanol, isopropylparaben, isobutylparaben, butylparaben[6] | 0.50 | 0.50 | 0.50 | 0.50 |

[1]Keltrol CG-T xanthan gum available from CP Kelco
[2]Rita GMS glyceryl stearate available from Rita Corp.
[3]Procol CS-20-D cetearyl alcohol available from Protameen Chemicals
[4]Rita CCT caprylic/capric triglyceride available from Rita Corp.
[5]Aculyn ™ 44 copolymer available from The Dow Chemical Company
[6]Liquapar ™ PE broad spectrum antimicrobial system available from Ashland CIELAB Measurements The skin care formulations according to Comparative Examples FB2 and FC2 and Examples F2-3 were each evaluated for CIE L*a*b* color space. A film of each of the skin care formulations was drawn down on a black/white drawdown card.

The drawdown film of each skin care formulation was prepared on a Leneta Form 2A black/white drawdown card using a BYK 3 MIL wet film applicator. The drawdown films were then allowed to air dry in ambient conditions for at least 12 hours. The CIE L*a*b* values for each skin care formulation was then measured on the white card only using a BYK Spectro-guide. The results are provided in TABLE 7.

TABLE 7

| Material | L* value | a* value | b* value |
|---|---|---|---|
| Blank Card | 90.29 | −0.63 | 5.07 |
| Comparative FB2 | 90.82 | −0.51 | 4.51 |
| Comparative FC2 | 91.55 | −0.50 | 3.36 |
| Example F2 | 84.96 | 8.10 | 18.96 |
| Example F3 | 87.89 | 4.20 | 11.97 |

The L* value represents the degree of lightness (i.e., whiteness) in terms of skin care applications. The multistage polymer particle (non-colored) has a very high L* value, which would be perceived as over-white and unnatural. The inventive multistage colored polymer particles on the other hand has a significantly lower L* value, which would be perceived more natural in appearance when applied to skin. Further, Example F3 demonstrates the customizability of outcome by blending the inventive multistage colored polymer particles with non-colored multistage polymer particles in the skin care formulation.

The a* value represents the red/green component colors with red at positive a* values and green at negative a* values. In terms of skin care, reddish or pinkish skin tones are generally perceived as appearing natural and healthy. As can be seen from the results, the skin care formulation of Example F2 comprising the multistage colored polymer particles has a significantly higher a* value compared with the other skin care formulations. Example F3 demonstrates the customizability of outcome by blending the inventive multistage colored polymer particles with non-colored multistage polymer particles in the skin care formulation.

The b* value represents the yellow/blue component colors with yellow at positive b* values and blue at negative b* values. In terms of skin care, the yellow color element makes up natural and healthy pinkish skin tones, which could be varied among populations. As can be seen from the results, the skin care formulation of Example F2 comprising the multistage colored polymer particles has a significantly higher b* value compared with the other skin care formulations. Example F3 demonstrates the customizability of outcome by blending the inventive multistage colored polymer particles with non-colored multistage polymer particles in the skin care formulation.

We claim:

1. A method of treating a selected area of skin, comprising:
   providing a skin care formulation; wherein the skin care formulation comprises:
      a dermatologically acceptable carrier;
      an optional additive; and
      0.01 to 10 wt %, based on weight of the skin care formulation, of a multistage colored polymer particle, comprising:
         (i) a core, wherein the core comprises, as polymerized units, 20 to 60 wt %, based on weight of the core, of a monoethylenically unsaturated carboxylic acid core monomer; and 40 to 80 wt %, based on weight of the core, of a non-ionic ethylenically unsaturated core monomer;
         (ii) an inner shell, wherein the inner shell comprises, as polymerized units, 90 to 99.9 wt %, based on weight of the inner shell, of a non-ionic ethylenically unsaturated inner shell monomer; 0.01 to 9.95 wt %, based on weight of the inner shell, a monoethylenically unsaturated carboxylic acid inner shell monomer; 0 to 9.99 wt %, based on weight of the inner shell, of an aliphatic inner shell monomer selected from the group consisting of allyl acrylate, allyl methacrylate and mixtures thereof; and 0 to 10 wt %, based on weight of the inner shell, of a first polymerizable dye monomer;

(iii) an outer shell, wherein the outer shell comprises, as polymerized units, 15 to 99.5 wt %, based on weight of the outer shell, of a non-ionic ethylenically unsaturated outer shell monomer; 0.1 to 10 wt %, based on weight of the outer shell, of a monoethylenically unsaturated non-carboxylic acid outer shell monomer; 0 to 10 wt %, based on weight of the outer shell, of a second polymerizable dye monomer; and 0 to 70 wt %, based on weight of the outer shell, of an aliphatic outer shell monomer selected from the group consisting of allyl acrylate, allyl methacrylate and mixtures thereof;

wherein the core, when dry, contains at least one void; wherein the first polymerizable dye monomer and the second polymerizable dye monomer are the same or different; and wherein the multistage colored polymer particle comprises, as polymerized units, 0.015 to 8 wt %, based on weight of the multistage colored polymer particle, of the first polymerizable dye monomer and the second polymerizable dye monomer combined; and applying the skin care formulation to a selected area of skin.

2. The method of claim 1, wherein the skin care formulation delivers a skin care benefit when applied to the selected area of skin; wherein the skin care benefit includes at least one of providing a natural tone to the selected area of skin, enhancing the natural tone of the selected area of skin, providing a pinkish appearance to the selected area of skin, and enhancing the pinkish appearance of the selected area of skin.

3. The method of claim 2, wherein the inner shell comprises 0 wt %, based on weight of the inner shell, of the first polymerizable dye monomer.

4. The method of claim 3, wherein the second polymerizable dye monomer comprises at least one polymerizable moiety and at least one colorant moiety; wherein the at least one polymerizable moiety is selected from the group consisting of a polymerizable $C_{1-5}$ alkylacrylate moiety and a polymerizable acrylate moiety; and wherein the at least one colorant moiety is derived from an azo dye.

5. The method of claim 4, wherein the second polymerizable dye monomer is an acrylated chromophore of formula I

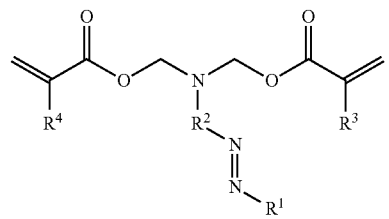

wherein $R^1$ is selected from the group consisting of an aryl group and a substituted aryl group;

wherein $R^2$ is selected from the group consisting of an aryl group and a substituted aryl group;

and wherein $R^3$ and $R^4$ are independently selected from the group consisting of a —H and a —$C_{1-5}$ alkyl group.

6. The method of claim 5, wherein $R^1$ is a phenyl group substituted with a —$NO_2$ group; wherein $R^2$ is selected from the group consisting of a phenyl group substituted with at least one of a —$CH_3$ group and a —N(H)C(O)$CH_3$ group; and wherein $R^3$ and $R^4$ are each a methyl group.

7. The method of claim 5, wherein the polymerizable dye monomer is an acrylated chromophore according of formula II

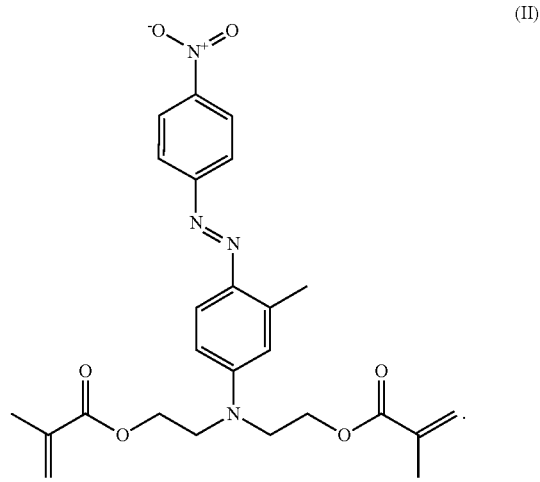

8. The method of claim 1, wherein the dermatologically acceptable carrier is a mixture of a $C_{1-4}$ straight or branched chain alcohol and water.

9. The method of claim 1, wherein the dermatologically acceptable carrier is a mixture of water and at least one of methyl alcohol, ethyl alcohol and isopropyl alcohol.

* * * * *